(12) United States Patent  (10) Patent No.: US 6,800,070 B2
Mazidji et al.  (45) Date of Patent: Oct. 5, 2004

(54) LOCKABLE TRANQUILIZER BRACELET

(76) Inventors: George Mazidji, 12 Rue Charles Chabert, 26200 Montelimar (FR); Vera M. Mansour, 3301 Clifolen Dr., Tallahassee, FL (US) 32309

( * ) Notice: Subject to any disclaimer, the term of this patent is extended or adjusted under 35 U.S.C. 154(b) by 0 days.

(21) Appl. No.: 10/289,759

(22) Filed: Nov. 7, 2002

(65) Prior Publication Data

US 2004/0092874 A1 May 13, 2004

(51) Int. Cl.$^7$ .......................... A61M 37/00; A61M 5/32
(52) U.S. Cl. .................... 604/147; 604/890.1; 604/179
(58) Field of Search .......................... 604/890.1–892.1, 604/191, 192, 244, 249, 174, 179, 181, 188, 201, 203, 146, 147, 196, 239, 272; 340/539.11, 539.13, 572.9, 572.1, 573.1, 573.4; 379/38

(56) References Cited

U.S. PATENT DOCUMENTS

| | | | | |
|---|---|---|---|---|
| 3,841,328 A | * | 10/1974 | Jensen | 604/135 |
| 3,964,481 A | * | 6/1976 | Gourlandt et al. | 604/152 |
| 4,214,584 A | * | 7/1980 | Smirnov et al. | 604/135 |
| 4,237,876 A | * | 12/1980 | Rumph et al. | 128/884 |
| 5,014,040 A | * | 5/1991 | Weaver et al. | 340/568.1 |
| 5,064,413 A | * | 11/1991 | McKinnon et al. | 604/70 |
| 5,115,223 A | * | 5/1992 | Moody | 340/573.1 |
| 5,135,479 A |   | 8/1992 | Sibalis et al. | |
| 5,235,320 A | * | 8/1993 | Romano | 340/539.11 |
| 5,310,404 A |   | 5/1994 | Gyory et al. | |
| 5,545,143 A |   | 8/1996 | Fischell | |
| 5,562,613 A |   | 10/1996 | Kaldany | |
| 5,800,420 A |   | 9/1998 | Gross et al. | |
| 5,807,375 A |   | 9/1998 | Gross et al. | |
| 5,820,622 A |   | 10/1998 | Gross et al. | |
| 5,860,957 A |   | 1/1999 | Jacobsen et al. | |
| 5,867,103 A | * | 2/1999 | Taylor, Jr. | 340/573.4 |
| 5,997,501 A |   | 12/1999 | Gross et al. | |
| 6,160,481 A | * | 12/2000 | Taylor, Jr. | 340/573.4 |
| 6,247,485 B1 |   | 6/2001 | Rossi et al. | |
| 6,349,232 B1 |   | 2/2002 | Gordon | |
| 2003/0062446 A1 | * | 4/2003 | Arias | 244/118.5 |

* cited by examiner

Primary Examiner—Anhtuan T. Nguyen
(74) Attorney, Agent, or Firm—John Wiley Horton (57) ABSTRACT

A tranquilizer bracelet which can be locked onto A wearer's wrist. The bracelet contains A power source, an electronic control module, and means for injecting A tranquilizing agent into the wearer. Instructions can be sent to the control module remotely, such as by using radio transmissions. The bracelet is provided with A lock to secure it to the wrist. It can only be opened using A mechanical key or electronic code. Thus, once the bracelet is installed, it cannot be removed by the wearer. In the event that tranquilization is necessary, A remote signal is sent to the control module. The signal activates A mechanism within the bracelet which causes the injection of the tranquilizing agent. Anti-tampering mechanisms are also provided, which will produce an alert signal if the bracelet is somehow removed by the wearer.

15 Claims, 9 Drawing Sheets

LOCKABLE TRANQUILIZER BRACELET

CROSS-REFERENCES TO RELATED APPLICATIONS

Not Applicable.

STATEMENT REGARDING FEDERALLY SPONSORED RESEARCH OR DEVELOPMENT

Not Applicable.

MICROFICHE APPENDIX

Not Applicable

BACKGROUND OF THE INVENTION

1. Field of the Invention.

This invention relates to the field of drug injection devices. More specifically, the invention comprises a bracelet which can be locked onto a wearer's wrist. The bracelet can then be remotely controlled in order to inject a tranquilizer into the wearer.

2. Description of the Related Art.

Devices for injecting pharmaceutical products into people are well known in the prior art. In recent years, wearable injection devices have been developed. These include wearable bracelets. Most of the devices intended for human use are controlled by the wearer, using keypads or buttons. Other devices, intended for animal use, incorporate radio receivers so that they can be remotely controlled.

BRIEF SUMMARY OF THE INVENTION

The present invention comprises a tranquilizer bracelet which can be locked onto a wearer's wrist. The bracelet contains a power source, an electronic control module, and means for injecting a tranquilizing agent into the wearer. Instructions can be sent to the control module remotely, such as by using radio transmissions. The bracelet is provided with a lock to secure it to the wrist. It can only be opened using a mechanical key or electronic code. Thus, once the bracelet is installed, it cannot be removed by the wearer.

In the event that tranquilization is necessary, a remote signal is sent to the control module. The signal activates a mechanism within the bracelet which causes the injection of the tranquilizing agent. Anti-tampering mechanisms are also provided, which will produce an alert signal if the bracelet is somehow removed by the wearer.

| REFERENCE NUMERALS IN THE DRAWINGS | | | |
|---|---|---|---|
| 10 | tranquilizer bracelet | 12 | tranquilizer assembly |
| 14 | lock assembly | 16 | band |
| 18 | rotary lock | 20 | keyhole |
| 22 | receiver | 24 | band attachment |
| 26 | pawl | 28 | latching notches |
| 30 | alternate lock assembly | 32 | magnetic encoder |
| 34 | recharge connector | 36 | chassis |
| 38 | lockable cover | 40 | injector assembly |
| 42 | gas cartridge | 44 | controller |
| 46 | battery | 48 | antenna |
| 50 | gas cartridge receiver | 52 | injector receiver |
| 54 | controller receiver | 56 | solenoid valve |
| 58 | gas conduit | 60 | hole |
| 62 | electrical conduit | 64 | loop anchor |
| 66 | piercable diaphragm | 68 | adjustment loop |
| 70 | male thread | 72 | injector body |
| 74 | retractor spring | 76 | piston |
| 78 | needle | 80 | piercable seal |
| 82 | needle cylinder | 84 | tranquilizer |
| 86 | inlet hole | 88 | piercer |
| 90 | injector hole | | |

DETAILED DESCRIPTION OF THE INVENTION

The present invention seeks to provide a means for tranquilizing dangerous individuals via the use of a remote controlling mechanism. The invention has application to airline hijackers, prisoners during transfer, and dangerous mental patients, among others.

Figure 1:
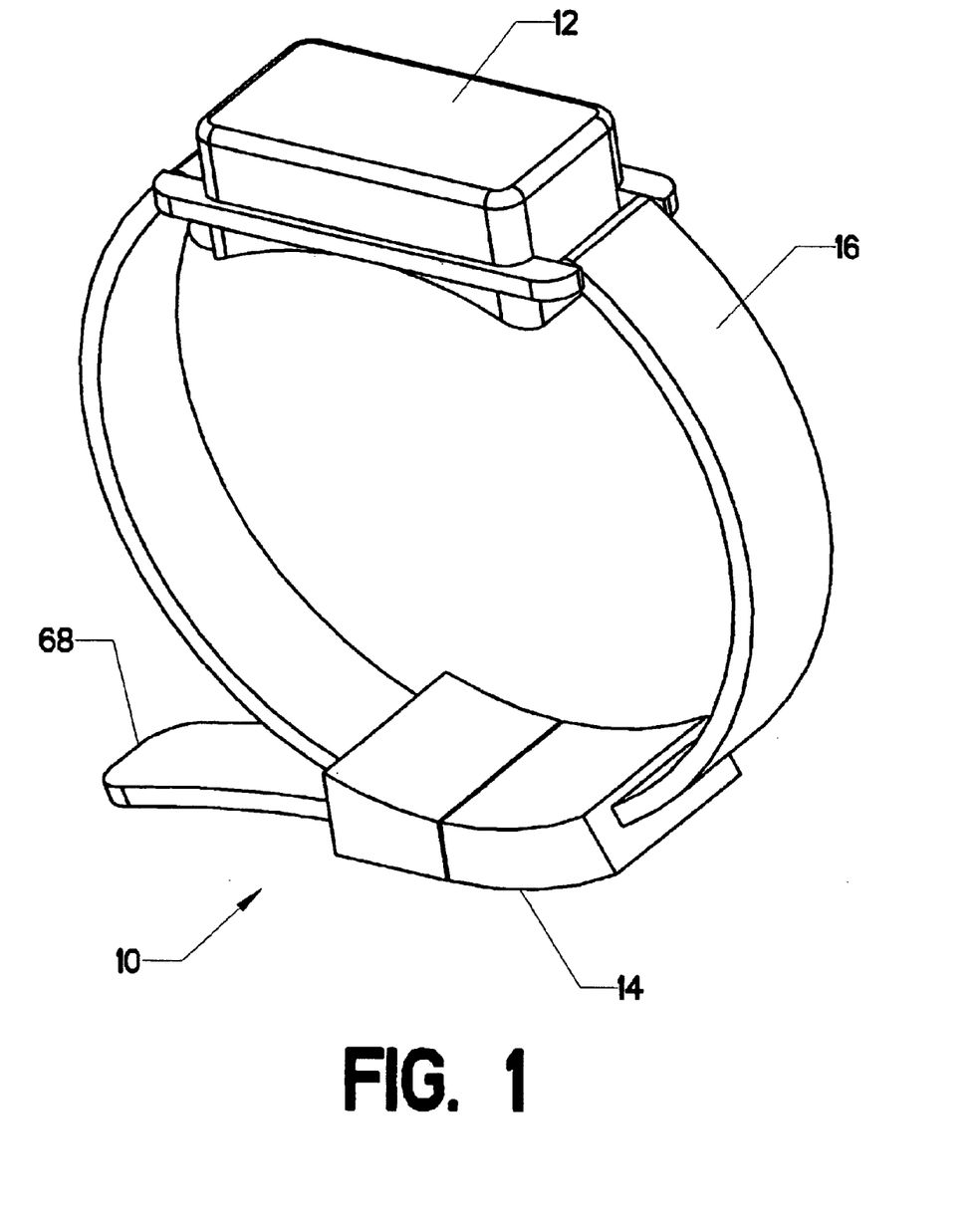
FIG. 1 is an isometric view, showing the present invention.

FIG. 1 shows an overall view of the present invention—denoted as tranquilizer bracelet 10. Tranquilizer assembly 12 is configured to rest atop a wearer's wrist, in much the same fashion as a watch body. Band 16 then encircles the wrist like a bracelet. Band 16 is bisected by lock assembly 14.

Figure 2:
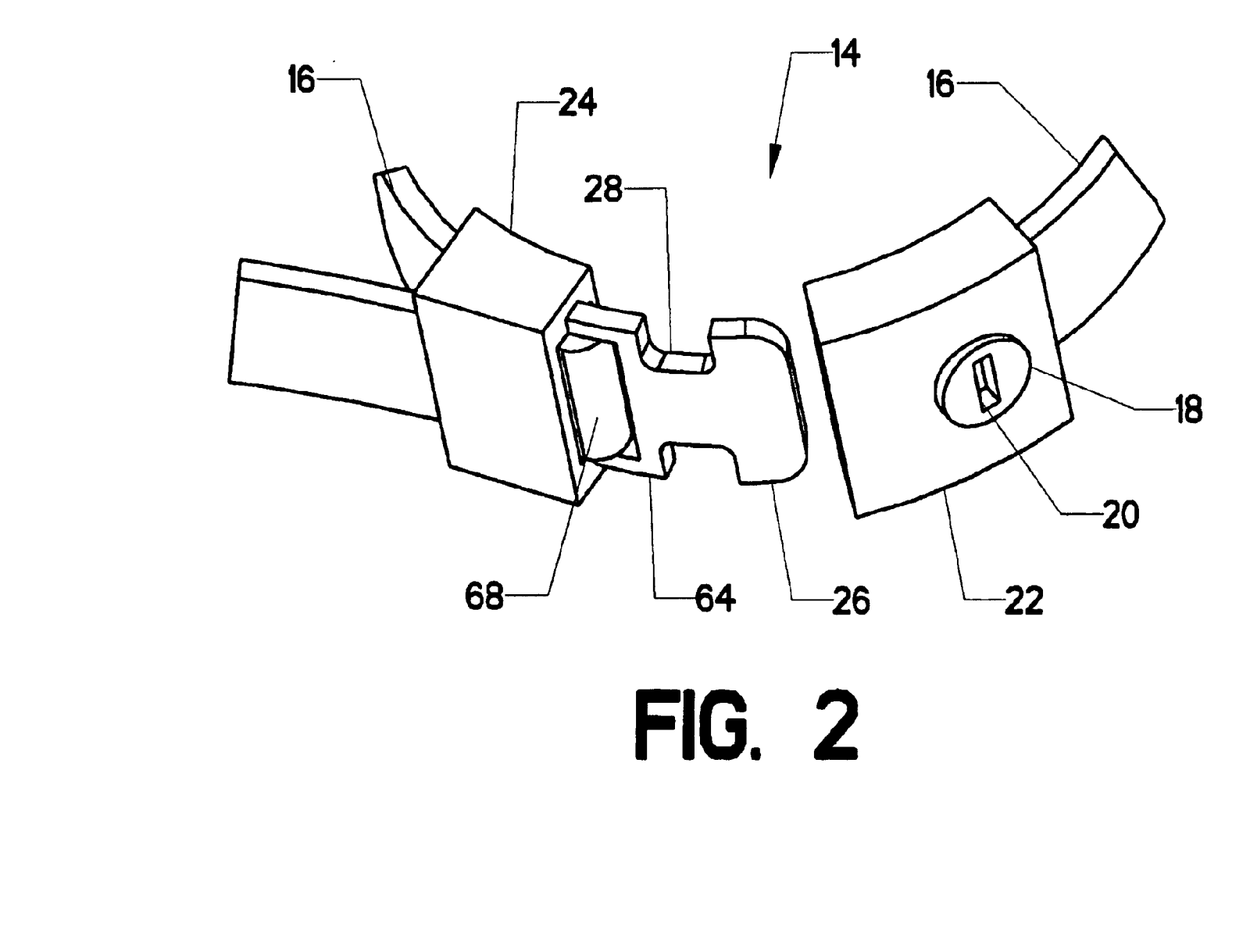
FIG. 2 is an isometric detail view, showing the locking mechanism.

FIG. 2 shows lock assembly 14 in its opened state (with band 16 actually being bisected into two segments). Band attachment 24 is affixed to one portion of band 16. Pawl 26 extends outward from this section. Pawl 26 contains engagement features—latching notches 28. In order to lock the invention in place, pawl 26 is inserted into receiver 22 as shown by the arrow. A separate key is then inserted in key hole 20 and used to rotate rotary lock 18. This rotation causes latching mechanisms within receiver 22 to move into engagement with latching notches 28, thereby securing band attachment 24 to receiver 22. Many different latching mechanisms could be employed. As the particular mechanism selected is not important to the present invention, and since they are well known in the art, these mechanisms have not been illustrated in greater detail.

The reader will appreciate that the diameter of band 16 must be sized to fit snugly over the wrist of the wearer, so that the wearer cannot remove the bracelet without the separate key. Referring briefly back to FIG. 1, adjustment loop 68 is provided for this purpose. Looking now at FIG. 2, the reader will observe that a portion of adjustment loop 68 extends through band attachment 24, where it loops around loop anchor 64 (a portion of pawl 26). When lock assembly 14 is in the unlocked state, the length of adjustment loop 68 can be altered in order to fit the wearer's wrist. Once lock assembly 14 is locked, however, adjustment loop 68 is mechanically locked in position, so that the wearer can no longer adjust the length of the band. Thus, although the bracelet is adjustable to fit different wearers, only the individual having the key can remove it in order for it to be adjusted.

Figure 3:
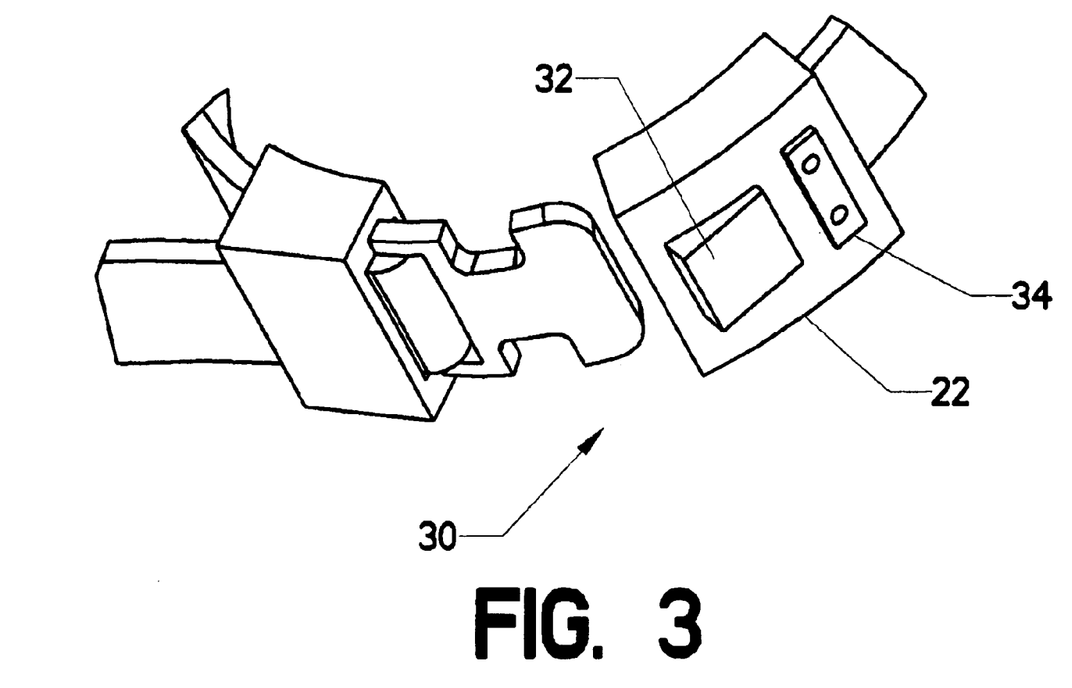
FIG. 3 is an isometric view, showing an alternate embodiment of the locking mechanism.

Those skilled in the art will know that a mechanical lock such as shown in FIG. 2 can sometimes be picked. It may therefore be desirable to use other types of locks. It may well be desirable to have locks that are responsive to a digital signal (whether provided via magnetic encoding, optical transmission, or other means). These locks have an advantage in that they are difficult to mechanically defeat, and in that the digital combination can be frequently changed. FIG. 3 shows alternate lock assembly 30, which incorporates a magnetic-type lock. Magnetic encoder 32 receives remote signals from a magnetic "key", when the key is passed over it. Assuming the appropriate signal is received, electrically-powered mechanisms within receiver 22 actuate to engage or disengage pawl 26. A power source—such as a battery—must be provided. This source can be located within receiver 22, or can be remotely located within tranquilizer assembly 12. If it is located within receiver 22, it is preferable to provide recharge connector 34 so that the battery can be recharged rather than replaced.

Figure 4:
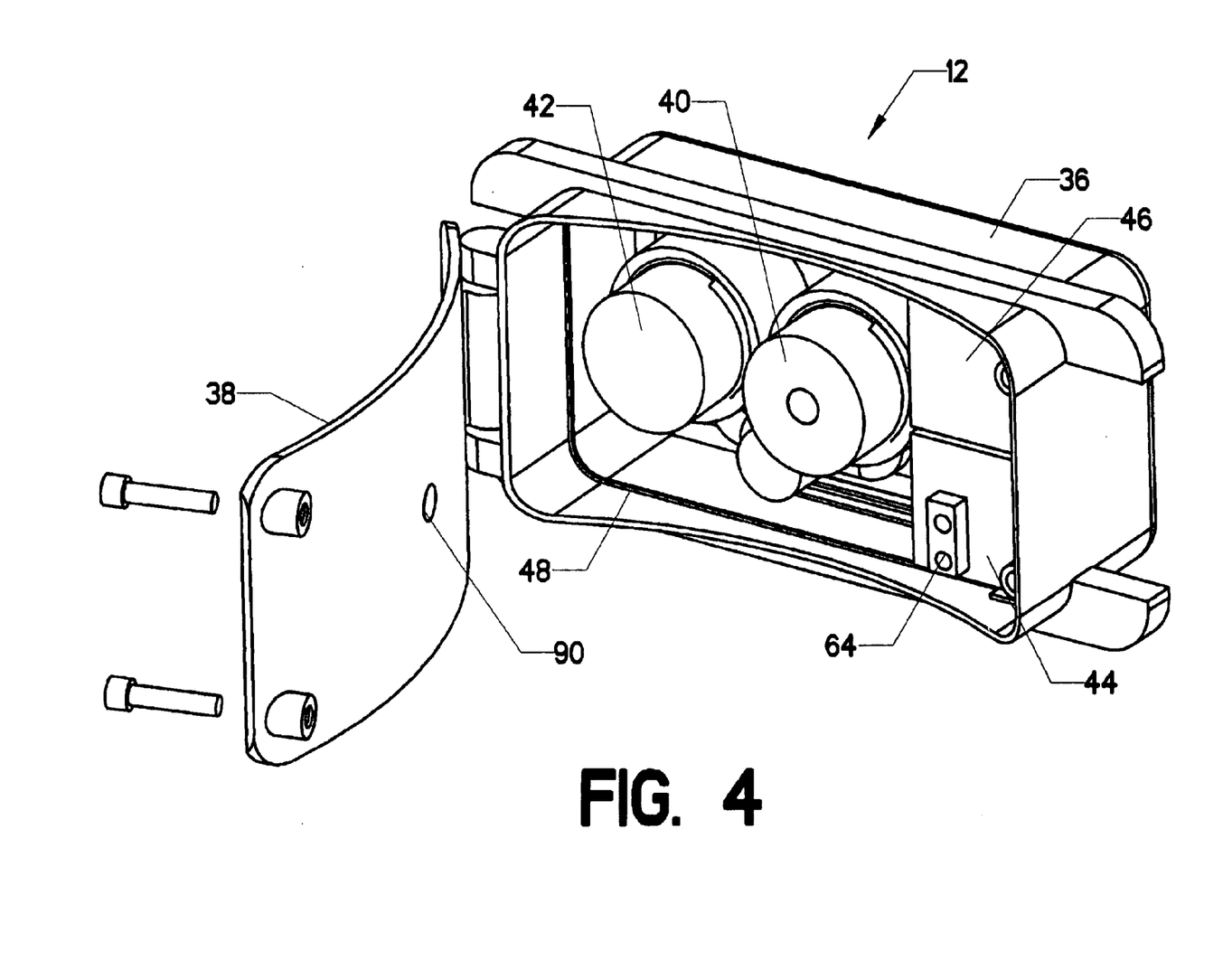
FIG. 4 is an isometric view, showing the internal component of the bracelet.

FIG. 4 shows tranquilizer assembly 12 from a different perspective. The side facing the viewer would be the side normally pressed against the wearer's wrist. Lockable cover 38 is shown in the open position. It is normally secured to chassis 36 by two screws or other prior art fastening means. Those skilled in the art will note that it is not possible to remove the fasteners while the bracelet is locked to the wearer's wrist. However, once the bracelet is removed, it is easy to open lockable cover 38 and thereby gain access to the components inside chassis 36.

Figure 5:
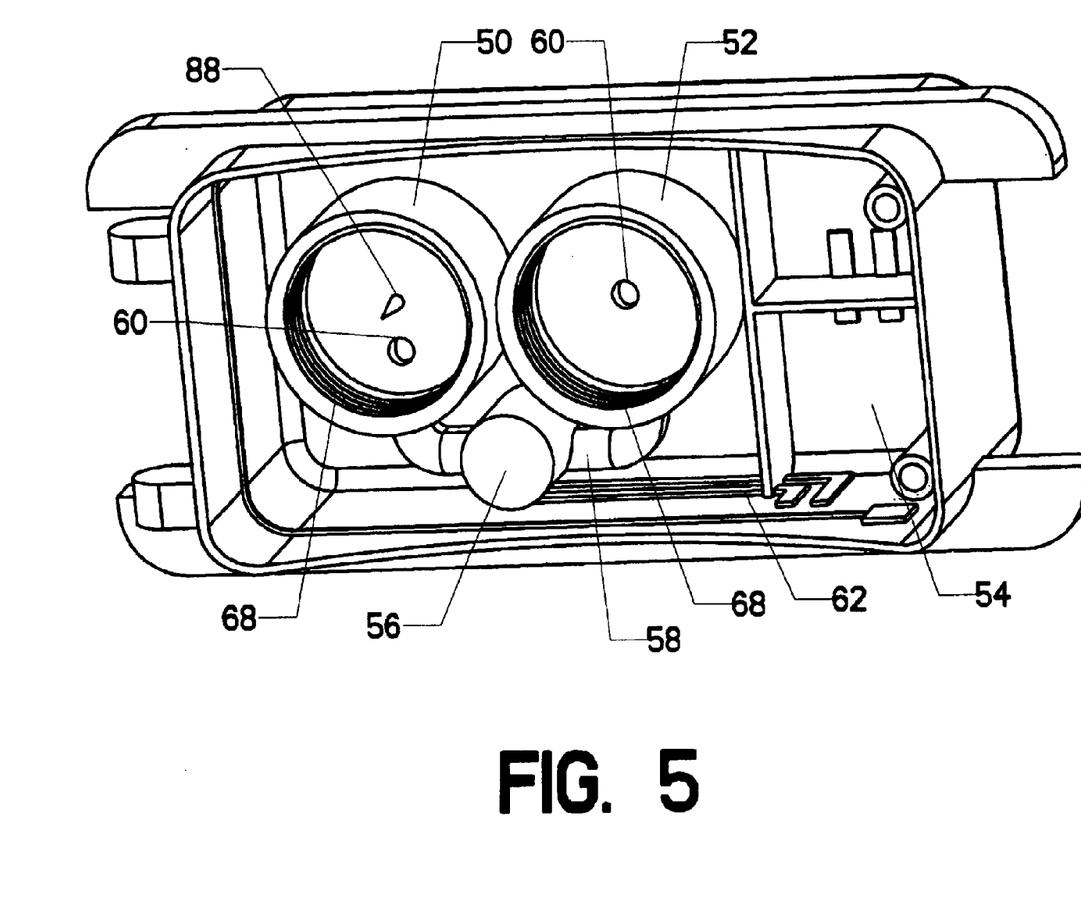
FIG. 5 is an isometric view, showing more detail of the internal components.
Figure 6:
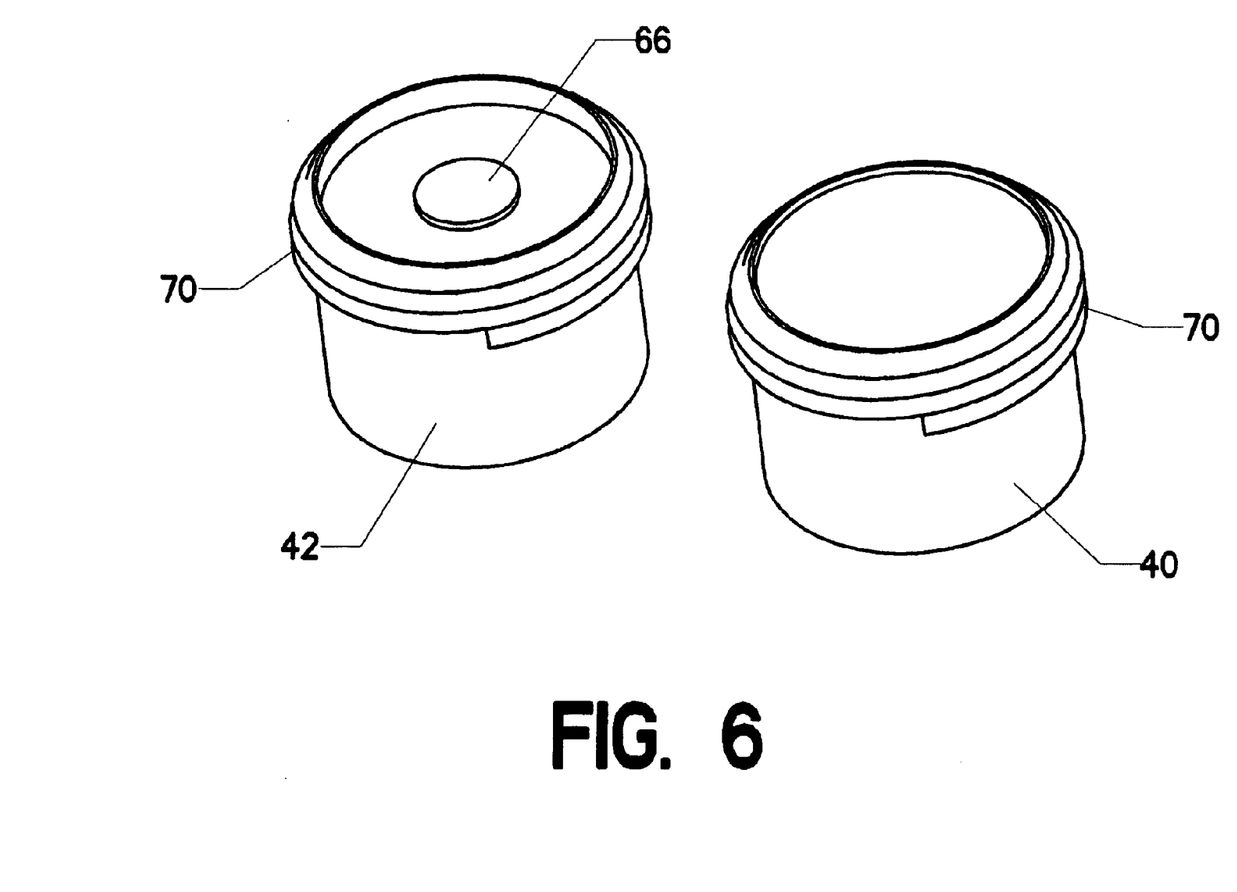
FIG. 6 is an isometric view, showing additional components.

Four major components are contained therein: gas cartridge 42, injector assembly 40, battery 46, and controller 44. Antenna 48 and recharge connector 64 are also provided. FIG. 5 shows the same view with the major components removed. FIG. 6 shows gas cartridge 42 and injector assembly 40 separately. Both these components are equipped with male thread 70 near the upper end. Gas cartridge 42 also has piercable diaphragm 66.

Returning now to FIG. 5, the reader will observe that gas cartridge receiver 50 and injector receiver 52 are both equipped with female thread 68. Gas cartridge receiver 50 is also equipped with piercer 88. When gas cartridge 42 is threaded into gas cartridge receiver 50, piercer 88 pierces piercable diaphragm 66, thereby venting the gas pressure within gas cartridge 42 through hole 60 in gas cartridge receiver 50 and into gas conduit 58. The gas pressure is checked from further progress via solenoid valve 56. Thus, via the operations just described, a pressurized gas source is connected to solenoid valve 56.

Injector assembly 40 threads into injector receiver 52. Injector receiver 52 opens into another hole 60, which is connected to gas conduit 58 on the downstream side of solenoid valve 56. Thus, solenoid valve 56 regulates the flow of pressurized gas from gas cartridge 42 to injector assembly 40. Solenoid valve 56 is electrically connected to controller receiver 54 by electrical conduits 62. When controller 44 is plugged into controller receiver 54, a pair of contacts on the bottom of controller 44 make electrical contact with electrical conduits 62. Thus, controller 44 controls the operation of solenoid valve 56.

Controller 44 is also connected to battery 46 and to antenna 48. Those skilled in the art will know that these electrical connections, as well as the antenna itself, can be formed using flexible circuit boards, thereby eliminating the need for separate wires. The provision of antenna 48 allows controller 44 to better receive and transmit external radio signals.

Figure 7:
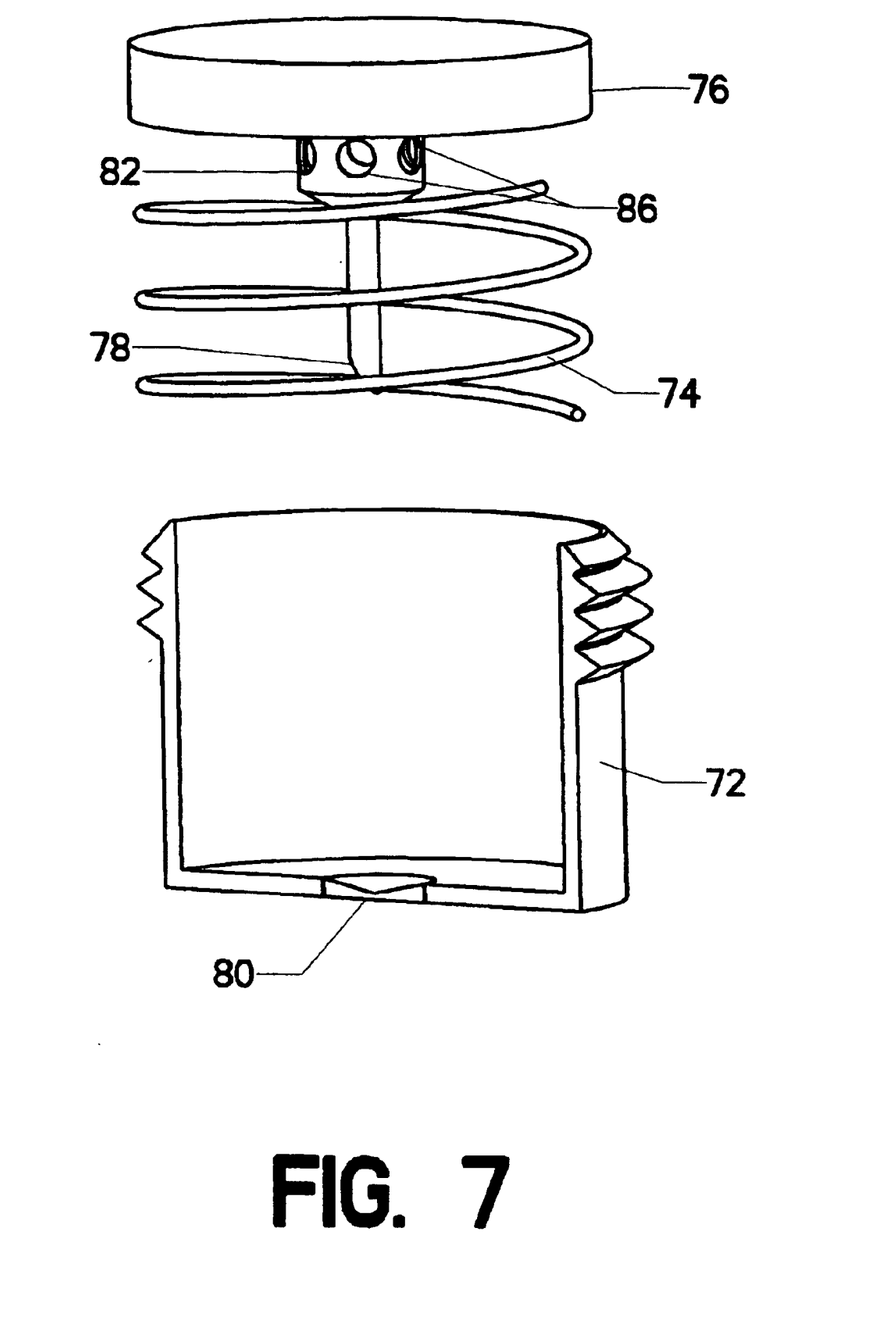
FIG. 7 is an isometric section view, showing the injector assembly.

FIG. 7 is an exploded sectional view, illustrating the details of injector assembly 40. The various components are housed within injector body 72, which is sectioned to aid visualization. Piston 76 is located at the top. This element provides a liquid-tight seal with the interior vertical wall of injector body 72. Needle cylinder 82 is connected to the underside of piston 76. Needle 78 descends downward from needle cylinder 82. Piercable seal 80 is centered in the bottom of injector body 72.

Figure 8:
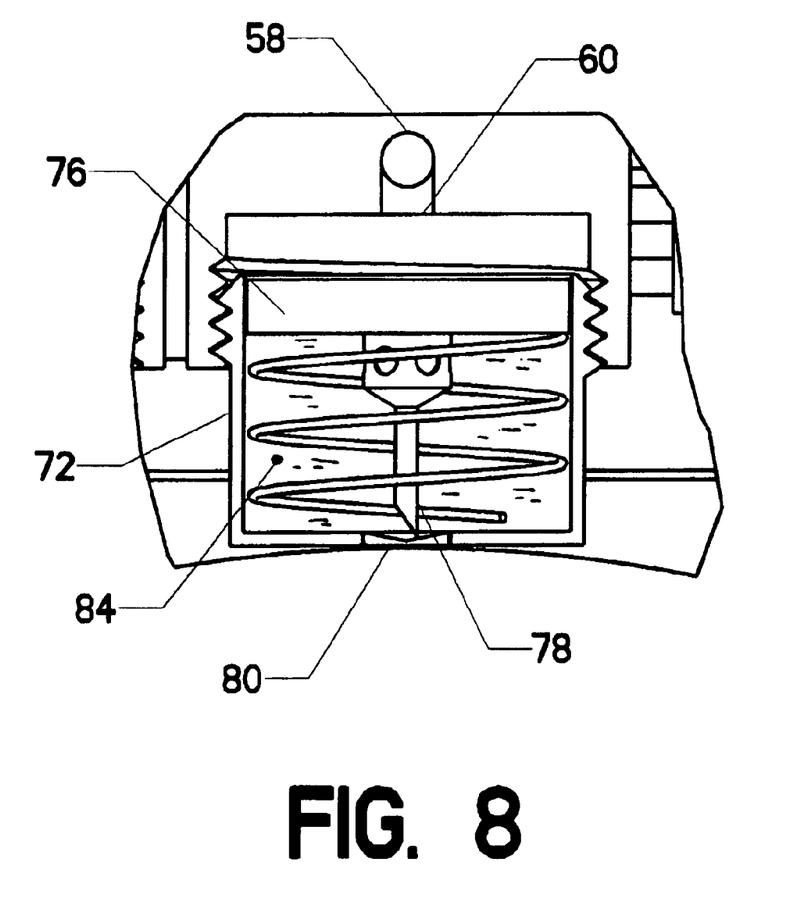
FIG. 8 is a section view, showing the injector assembly.
Figure 9:
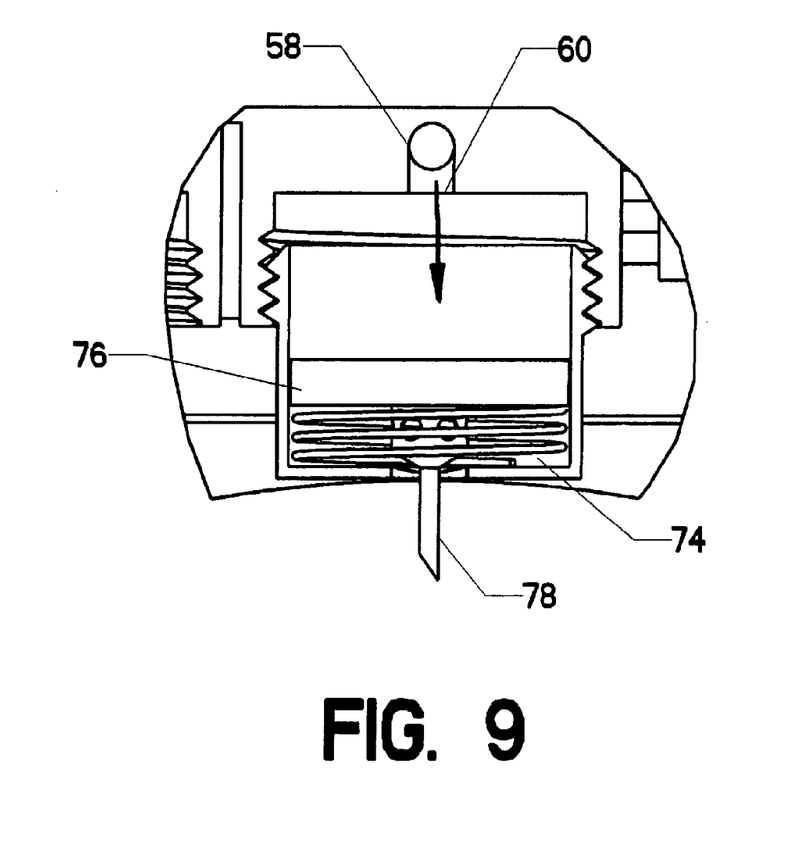
FIG. 9 is a section view, showing the injector assembly.

FIGS. 8 and 9 are sectional views showing the operation of injector assembly 40. In FIG. 8, piston 76 is in its "home" position. Needle cylinder 82 and needle 78 are hollow cylinders which are in fluid communication with each other. Additionally, needle cylinder 82 opens into a plurality of inlet holes 86. The bottom of needle 78 opens into a conventional injection hole. A reservoir of tranquilizer 84 (in liquid form) rests beneath piston 76. Return spring 74 also rests beneath piston 76. Injector assembly 40 can be stored for extended periods in this state, apart from the tranquilizer bracelet. Piston 76 seals the open top of injector body 72 and prevents contamination of the tranquilizing agent.

When the command is sent to trigger the injection cycle, controller 44 energizes solenoid valve 56, which provides gas pressure to the portion of gas conduit 58 shown in FIG. 8. This pressure flows through hole 60 into the area over piston 76, thereby driving piston 76 downward. As piston 76 descends, the tip of needle 78 pierces piercable seal 80. The pressure on tranquilizer 84 also causes it to flow into inlet holes 86 and down into the interior of needle 78.

FIG. 9 shows the assembly after piston 76 has been forced down to its lowest extent. The tip of needle 78 extends well below the device. Returning briefly to FIG. 4, the reader will appreciate that once it is deployed as shown in FIG. 9, needle 78 will protrude out through injector hole 90 and into the wrist of the user. Looking back at FIG. 9, those skilled in the art will therefore appreciate that the downward motion of piston 76 simultaneously causes (1) needle 78 to pierce the skin of the wearer and descend to an appropriate injection depth; and (2) the injection of tranquilizer 84 through the open lower extreme of needle 78. Once this has occurred, controller 44 closes solenoid valve 56, thereby removing the gas pressure. Retractor spring 74 then forces piston 76 back up, thereby retracting needle 78 from the wearer's wrist.

Looking back at FIGS. 5 and 6, those skilled in the art will appreciate that gas cartridge 42 and injector assembly 40 are configured to be easily replaced as complete modular units. This arrangement is preferable, since the gas cartridge will lose pressure over time and the tranquilizing agent may have a limited shelf life. Rather than forcing the user to refill the tranquilizer reservoir or repressurize the gas reservoir, the user simply screws out the old units and screws in the new ones.

Those skilled in the art will also realize that other mechanisms could be substituted for the use of gas pressure in actuating piston 76. As one example, an electrical solenoid could be positioned above piston 76 in order to drive piston 76 downward.

As mentioned previously, it is important that the wearer not be able to remove the bracelet. It should only be removed by authorized personnel. Thus, the material used for band 16 must be cut-resistant. Braided steel ribbons embedded in a rubber jacket are particularly effective. Likewise, lock assembly 14 must be strong. However, it is anticipated that even the strongest securing mechanisms can be defeated by certain resourceful individuals. Therefore, another protection device is preferable.

As described previously, controller 44 is configured to receive external radio signals—such as the command triggering the injection cycle. Controller 44 can also be used, however, to transmit a radio signal indicating that the wearer is attempting to remove the bracelet. Returning now to FIG. 1, those skilled in the art will realize that it is very easy to provide a conductive electrical path around band 16. A circuit within controller 44 can therefore be created to monitor the conductivity of this path. If lock assembly 14 is opened, an open circuit will result. Likewise, if band 16 is cut, an open circuit will result. Controller 44 can be configured to transmit a signal indicating that the wearer has removed the bracelet.

A further refinement is possible. If, as an example, band 16 is made of the aforementioned braided steel ribbon, a circuit can be configured to monitor the total resistance of that ribbon. If the wearer then begins sawing through the ribbon, the resistance value will increase. Controller 44 can then be configured to transmit a warning signal while the wearer is still attempting to cut the band, thereby allowing a guard or other supervisory person to initiate the tranquilization cycle.

Other anti-tampering provisions are possible. Referring now to FIG. 4, lockable cover 38 can be made of a conductive material such as aluminum. An electrical temperature sensor can then be placed on its internal surface and electrically connected to controller 44. The temperature sensor would sense the normal human body temperature present when the device is present on the wearer's wrist. If the wearer removes the device, the sensor would detect the dropping temperature of lockable cover 38 (so long as the ambient temperature is below human body temperature). Controller 44 can then transmit a warning signal.

As the device employs electrical circuitry, it is important to make it water-tight or at least water resistant. Still referring to FIG. 4, those skilled in the art will realize that a sealing gasket can be added to the perimeter of lockable cover 38 in order to accomplish this goal.

The particular tranquilizing agent selected for use with the invention is not critical, so long as it is fast-acting. The delivery device disclosed also requires the tranquilizing agent to be stored in liquid form. One suitable agent is curare.

Now that the detailed operation of the injector bracelet itself has been described, the way in which it fits into a larger integrated system can be explained. Although many applications for the device are possible, the situation of an airline hijacking will be used to illustrate.

All passengers on a commercial airliner would be fitted with tranquilizer bracelet 10 prior to boarding the flight. The bracelets would be locked in place so that the passengers could not remove them. Each controller 44 would be encoded with a passenger-specific code. These codes would be correlated to seat assignments. Sensors would also be placed in the aircraft in order to detect whether a passenger is in his or her seat. These sensors would exchange electronic proximity signals with the controllers 44. All the sensors would be in electronic communication with a central control unit. Likewise, all the bracelets can be in electronic communication with the central control unit.

Video monitoring of the passenger cabin would be maintained by the flight crew (as well as visual monitoring by the flight attendants). In the event of trouble with a passenger or passengers, the flight crew would announce that all passengers must immediately return to their seats. The central control unit would then be able to determine which passengers remain out of their seats. A radio command can then be sent to initiate the tranquilization cycle for those passengers remaining out of their seats. In this fashion, any hijackers can be tranquilized.

In another embodiment, a motion detector could be included within tranquilizer assembly 12. In the event of trouble, the passengers would be instructed to remain still. A signal would then be sent to all the controllers 44 arming the bracelets so that they will initiate the tranquilization cycle if motion is detected. In this fashion, any hijackers continuing to move aggressively will be tranquilized.

Those skilled in the art will realize that the invention could be used in many different ways. The situation is much less complicated for the scenario of transporting a prisoner. In that scenario, only one tranquilizer bracelet 10 would be used—on the prisoner. Then a simple radio transmitter could be used to initiate the tranquilization cycle.

Although the preceding description contains significant detail regarding the novel aspects of the present invention, it should not be construed as limiting the scope of the invention, but rather as providing illustrations of the preferred embodiments. Thus, the scope of the invention should be fixed by the following claims, rather than by the examples given.

Having described my invention, we claim:

1. A tranquilizer bracelet for administering a dose of tranquilizer to a wearer through said wearer's wrist, comprising:

a. a tranquilizer assembly, having an inward facing side and an outward facing side, for use on said wrist, and containing a tranquilizing agent therein and means for injecting said tranquilizing agent into said wearer, including i. a hollow injector body containing said tranquilizing agent, having an open upper end and a closed lower end proximate said inward facing side;

ii. a piercable seal located in said closed lower end of said injector body;

iii. a piston, having an upper side and a lower side, slidably positioned within said hollow injector wherein said lower side is above said tranquilizing agent;

iv. a hollow needle, having an upper portion and a lower portion, wherein said upper portion is connected to said lower side of said piston, wherein said upper portion is pierced by an inlet hole, and wherein said lower portion opens into an injection hole;

v. a pressurized gas cartridge, having an upper end and a lower end, wherein said gas cartridge is located beside said hollow injector body with said lower end of said gas cartridge being proximate said inward facing side;

vi. a solenoid valve, having a first side and a second side, fluidly connected to said gas cartridge on said first side, and fluidly connected to said injector body above said piston on said second side;

b. a band, attached to said tranquilizer assembly and configured to encircle said wrist of said wearer so as to attach said tranquilizer assembly to said wrist with said inward facing side bearing against said wrist;

c. a lock assembly, located within said band, wherein said lock assembly can be unlocked in order to open said band and allow said tranquilizer bracelet to be placed on said wrist, and wherein said lock assembly can be locked in order to prevent said wearer from removing said tranquilizer bracelet; and d. control means for actuating said solenoid valve, so that said solenoid valve connects said gas cartridge to said injector body in order to create a downward mechanical force on said piston.

2. A tranquilizer bracelet as recited in claim 1, wherein said lock assembly comprises a mechanical lock which can be opened by a separate key.

3. A tranquilizer bracelet as recited in claim 1, wherein said lock assembly comprises an electronically actuated lock which can be opened by the use of a magnetic encoder.

4. A tranquilizer bracelet as recited in claim 1, wherein said lock assembly comprises an electronically actuated lock which can be opened by the transmission of a numeric code.

5. A tranquilizer bracelet as recited in claim 1, wherein said band and said lock assembly include a conductor passing completely around said wrist, so that said control means can sense when said band and said lock assembly encircling said user's wrist has been opened.

6. A tranquilizer bracelet as recited in claim 1, further comprising a temperature sensor capable of detecting the presence of said wearer's body heat, so that said control means can sense when said tranquilizer bracelet has been removed from said wearer.

7. A tranquilizer bracelet as recited in claim 1, wherein said band further comprises adjustment means allowing said band to be fitted tightly to said wrist, but wherein said adjustment means cannot be adjusted when said lock assembly is locked.

8. A tranquilizer bracelet as recited in claim 1, wherein said control means comprises an electronic controller responsive to signals received from an external source.

9. A tranquilizer bracelet as recited in claim 1, wherein said control means comprises an electronic controller capable of transmitting signals to an external source.

10. A tranquilizer bracelet as recited in claim 1, further comprising a retractor spring, positioned to move said piston upward once said downward mechanical force on said piston is removed.

11. A tranquilizer bracelet as recited in claim 1, wherein said gas cartridge is easily removed from said tranquilizer bracelet and replaced by another of said gas cartridges, once said original gas cartridge is depleted.

12. A tranquilizer bracelet as recited in claim 11, wherein said hollow injector body, said tranquilizing agent, said piercable seal, said piston, and said hollow needle, are all contained within a modular injector assembly which can be easily removed from said tranquilizer bracelet and replaced by another of said modular injector assemblies, once said original modular injector assembly is depleted.

13. A tranquilizer bracelet as recited in claim 12, wherein said tranquilizer assembly contains an injector receiver for receiving and securing said modular injector assembly and a gas cartridge receiver for receiving and securing said gas cartridge.

14. A tranquilizer bracelet as recited in claim 13, wherein said tranquilizer assembly and said gas cartridge are accessible through a lockable door in said inward facing side of said tranquilizer assembly.

15. A tranquilizer bracelet as recited in claim 1, wherein said hollow injector body, said tranquilizing agent, said piercable seal, said piston, and said hollow needle, are all contained within a modular injector assembly which can be easily removed from said tranquilizer bracelet and replaced by another of said modular injector assemblies, once said original modular injector assembly is depleted.

* * * * *